United States Patent
Nekrassov et al.

(10) Patent No.: US 11,751,764 B2
(45) Date of Patent: Sep. 12, 2023

(54) MEASURING A POSTERIOR CORNEAL SURFACE OF AN EYE

(71) Applicant: ALCON INC., Fribourg (CH)

(72) Inventors: Daniil Nekrassov, Berlin (DE); Martin Gruendig, Rangsdorf (DE)

(73) Assignee: Alcon Inc., Fribourg (CH)

( * ) Notice: Subject to any disclaimer, the term of this patent is extended or adjusted under 35 U.S.C. 154(b) by 1062 days.

(21) Appl. No.: 16/406,828

(22) Filed: May 8, 2019

(65) Prior Publication Data
US 2019/0357767 A1 Nov. 28, 2019

Related U.S. Application Data

(60) Provisional application No. 62/675,429, filed on May 23, 2018.

(51) Int. Cl.
| | |
|---|---|
| A61B 3/107 | (2006.01) |
| A61B 3/103 | (2006.01) |
| A61B 3/14 | (2006.01) |
| A61B 3/00 | (2006.01) |
| G06T 7/00 | (2017.01) |
| H04N 7/18 | (2006.01) |

(52) U.S. Cl.
CPC .......... *A61B 3/107* (2013.01); *A61B 3/0025* (2013.01); *A61B 3/14* (2013.01); *G06T 7/0016* (2013.01); *H04N 7/181* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 5,870,167 A | 2/1999 | Knopp et al. | |
| 2001/0033362 A1* | 10/2001 | Sarver | A61B 3/1005 351/212 |
| 2009/0190093 A1 | 7/2009 | Tanassi et al. | |
| 2010/0060854 A1 | 3/2010 | Bille | |
| 2018/0125355 A1* | 5/2018 | Mrochen | A61B 3/0025 |
| 2021/0315452 A1* | 10/2021 | Neal | A61B 3/1015 |
| 2021/0325276 A1* | 10/2021 | Glasenapp | A61B 3/103 |

FOREIGN PATENT DOCUMENTS

EP 1462074 A1 9/2004

* cited by examiner

*Primary Examiner* — Samuel D Fereja

(57) ABSTRACT

In certain embodiments, a system for measuring the posterior corneal surface of the cornea comprises cameras and a computer. Each camera generates image data representing a part of the eye posterior to the cornea. The image data describes locations of features of the part. The computer stores a description of the shape of an anterior corneal surface of the cornea, and applies a ray-tracing process to determine the shape of the posterior corneal surface. The ray-tracing process comprises defining rays, where each ray is traced from a camera, through the anterior and posterior corneal surfaces, and to the part of the eye. Constraints for the rays are determined, where the constraints are calculated using the description of the shape of the anterior corneal surface and locations of the features in the image data. Parameters are optimized, and the optimized parameters describe the shape of the posterior corneal surface.

13 Claims, 3 Drawing Sheets

MEASURING A POSTERIOR CORNEAL SURFACE OF AN EYE

TECHNICAL FIELD

The present disclosure relates generally to ophthalmic measurements, and more specifically to measuring a posterior corneal surface of an eye.

BACKGROUND

The cornea of an eye has an anterior surface and a posterior surface that affect how light goes through the eye and ultimately affect the vision of the eye. The difference in refractive indices between air and the stroma at the anterior corneal surface is larger than the difference between the indices of the stroma and aqueous humor at the posterior corneal surface. Accordingly, the effect of the anterior corneal surface is larger relative to that of the posterior one. However, the effect of the posterior corneal surface is not, by any means, negligible. Optical coherence tomography (OCT), Scheimpflug, Purkinje, and slit lamp imaging devices can be used to measure the shape of the posterior corneal surface. However, these devices might not be favorable in certain situations. For example, OCT and Scheimpflug devices have moving components that can be expensive, and Purkinje devices can suffer from weak signals from the posterior part of the cornea.

BRIEF SUMMARY

In certain embodiments, a system for measuring the posterior corneal surface of the cornea of an eye includes cameras and a computer. Each camera generates image data representing a part of the eye posterior to the cornea. The image data describes locations of features of the part of the eye. The computer has a memory and one or more processors. The memory stores the image data from the cameras, and stores a description of the shape of an anterior corneal surface of the cornea. The processors apply a ray-tracing process to determine the shape of the posterior corneal surface. The ray-tracing process comprises defining rays, where each ray is traced from a camera, through the anterior corneal surface and the posterior corneal surface, and to the part of the eye. Constraints for the rays are determined. The constraints are calculated using the description of the shape of the anterior corneal surface and locations of the features in the image data. Parameters are optimized according to the constraints, and the optimized parameters describe the shape of the posterior corneal surface.

In certain embodiments, the processors determine the constraints for the rays by performing one or more of the following: (1) for each ray traced from a camera, calculating an anterior point where the ray intersects with the anterior corneal surface according to a position of the camera relative to the eye; (2) for each ray, calculating an anterior angle by which the anterior corneal surface refracts the ray according to the shape of the anterior corneal surface at an anterior point where the ray intersects the anterior corneal surface; (3) for each ray, calculating a posterior point where the ray intersects with the posterior corneal surface according to a position of the ray subsequent to the refraction by the anterior corneal surface; (4) assuming a shape of the posterior corneal surface; and for each ray, calculating a posterior angle by which the posterior corneal surface refracts the ray according to the assumed shape of the posterior corneal surface at a posterior point where the ray intersects the posterior corneal surface; and/or (5) for each feature: identifying the rays corresponding to that feature; and from the image data from at least two cameras, calculating one or more least distances among the rays.

In certain embodiments, the processors optimize the parameters according to the constraints by performing one or more of the following: (1) identifying values for the parameters, where the values optimize agreement between the image data from the cameras; (2) identifying values for the parameters, where the values minimize a plurality of least distances among the rays; and/or (3) identifying values for the parameters, where the values minimize a sum of a plurality of least distances among the rays. The processors further calculate the shape of the posterior corneal surface according to the optimized parameters.

In certain embodiments, a method for measuring the posterior corneal surface of the cornea of an eye comprises generating, by each of a plurality of cameras, image data representing a part of the eye posterior to the cornea. The image data describes locations of features of the part of the eye. A description of the shape of an anterior corneal surface of the cornea is accessed. A ray-tracing process is applied to determine the shape of the posterior corneal surface. The ray-tracing process includes defining rays, where each ray is traced from a camera, through the anterior corneal surface and the posterior corneal surface, and to the part of the eye. Constraints for the rays are determined, where the constraints are calculated using the description of the shape of the anterior corneal surface and locations of the features in the image data. Parameters are optimized according to the constraints, the optimized parameters describing the shape of the posterior corneal surface.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
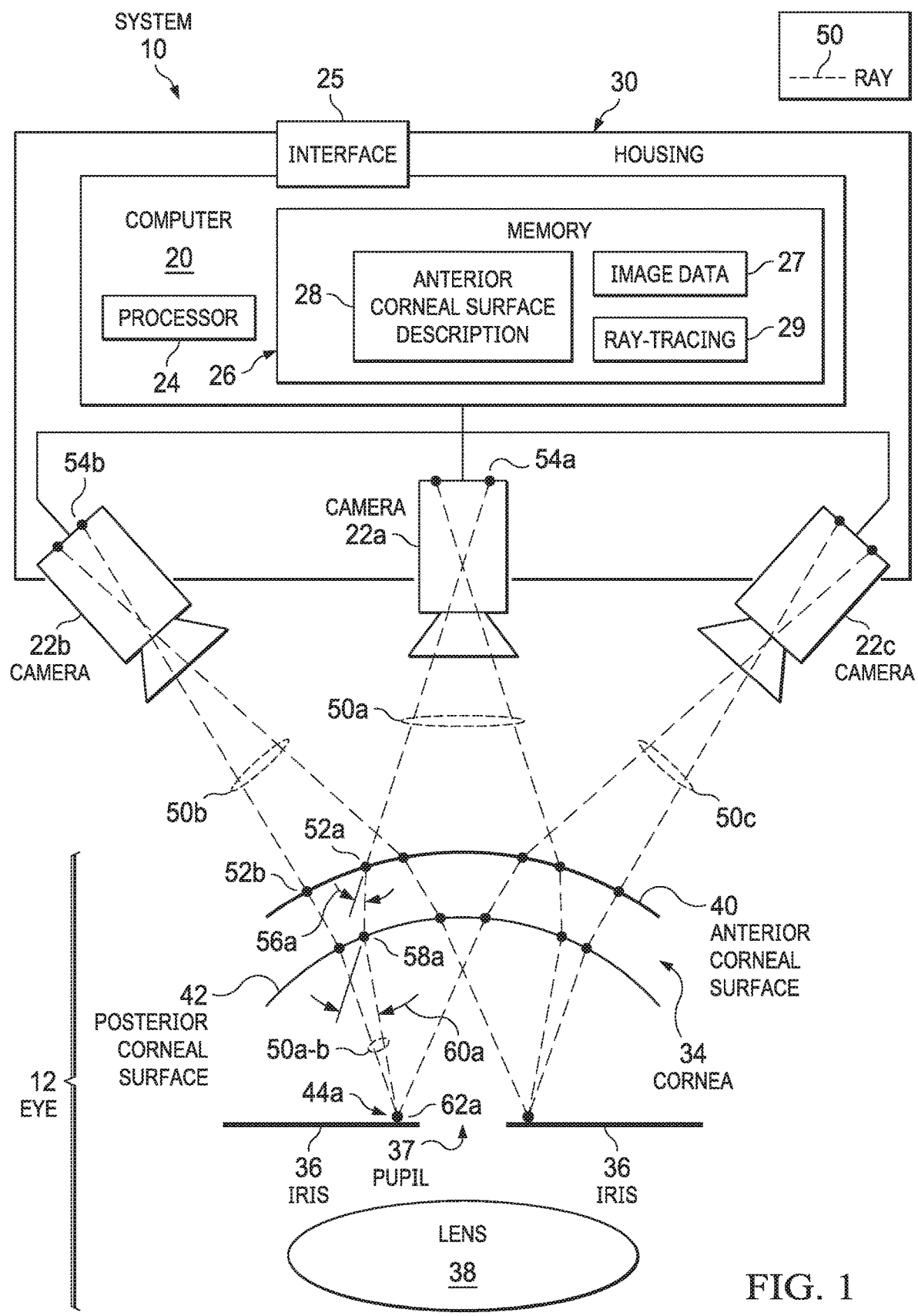
FIG. 1 illustrates an embodiment of a system that measures the posterior corneal surface of an eye.

FIG. 1 illustrates an embodiment of a system 10 that measures a posterior corneal surface of an eye 12. In certain embodiments, system 10 includes cameras that generate image data representing features of a part of eye 12 that is posterior to the cornea, e.g., the iris. A computer uses a ray-tracing process to determine the shape of the posterior corneal surface from the image data and the shape of the anterior corneal surface of eye 12.

In the illustrated example, system 10 includes a computer 20 coupled to at least two cameras 22 (22*a-c*). Computer 20 includes one or more processors 24, an interface 25, and a memory 26. Memory 26 stores data (such as image data 27 and a description of anterior corneal surface 28) and applications (such as a ray-tracing module 29). A housing 30 may contain at least a portion of one or more components of system 10. Eye 12, such as a human eye, includes a cornea 34, iris 36, pupil 37, lens 38, and other well-known parts. Cornea 34 has an anterior corneal surface 40 and a posterior corneal surface 42. While corneal topography systems and keratometers measure the shape of anterior corneal surface 40, system 10 measures the shape of posterior corneal surface 42.

Regarding system 10 in more detail, a camera 22 may be any suitable digital camera that captures an image of an object in digital memory. A digital image sensor (e.g., CCD or CMOS) of camera 22 detects light reflected from the object and generates a digital signal with image data that represents the reflected light. The image data can be stored and processed to be used in various ways. In some cases, the image data can be processed to display the image of the object. In other cases, the image data can be processed identify parts of the object represented in the image. For example, image data generated when capturing an image of eye 12 can be processed to identify landmark features of a part of eye 12, e.g., markings of iris 36. The landmark features may be used to align images from different cameras. Features are described in more detail with reference to FIG. 2.

Figure 2:
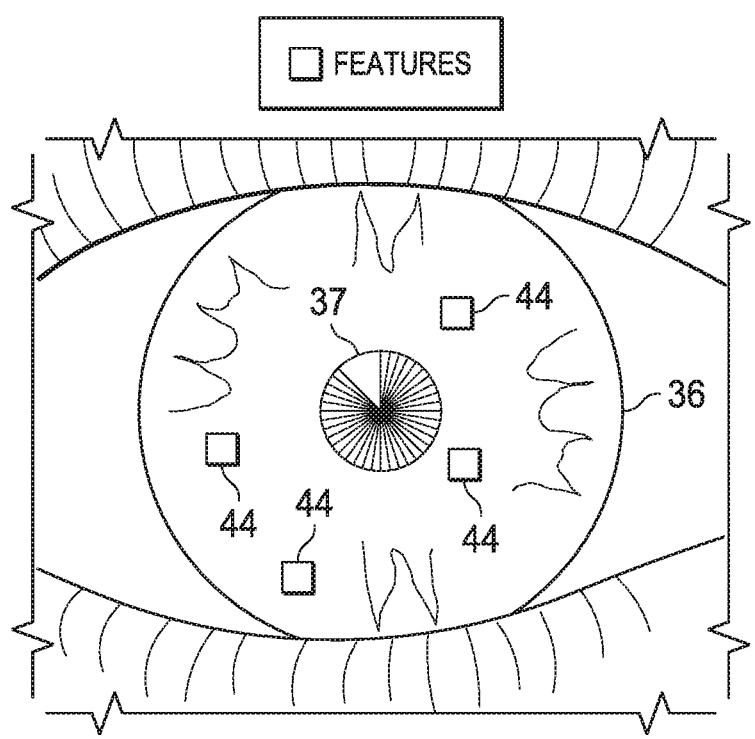
FIG. 2 illustrates an example of an image of an iris that can be used to align images from different cameras of the system of FIG. 1.

FIG. 2 illustrates an example of an image of iris 26 with features 44. A part of eye 12 may have features 44 that operate as landmarks to establish their location and can be used to align (or register) images from different cameras 22. Any suitable part of eye 12 may be used, e.g., the iris or pupil edge. A feature 44 of a part may be a marking that can be identified in an image of the part. In the illustrated example, iris 36 has markings of color and texture selected as features 44.

Returning to FIG. 1, system 10 includes cameras 22a-c. Camera 22a is an on-axis camera, where the optical axis of camera 22a substantially coincides with an axis (e.g., optical or visual) of eye 12. Cameras 22b-c are off-axis cameras, where the optical axis of each camera 2b-c is at an angle with an axis of eye 12. The angle may have any suitable value, e.g., a value within the range of 10 to 30, 30 to 40, or 40 to 60 degrees. In general, system 10 may have any suitable number of cameras 22. Cameras 22 may be all off-axis cameras or may include an on-axis camera.

Memory 26 stores image data 27 and a description of anterior corneal surface 28. Image data 27 may be image data received from cameras 22. Description of anterior corneal surface 28 describes the shape of anterior corneal surface 40. The description may be in the form of a map of the surface, such as an axial, tangential, refractive power, or elevation map. For example, the description may provide the surface elevation and surface normal at different points of anterior corneal surface 28, where interpolation may be used to calculate the elevation and normal at other points. Description 28 may be generated by a corneal topography system (e.g., a Placido disc system) or a keratometer.

Memory 26 stores ray-tracing module 28. Processors 24 use ray-tracing module 28 to apply a ray-tracing process. Ray-tracing is typically based on an eye model (e.g., Gullstrand, Navarro, Liou and Brennan, and Emsley) and measurements of an eye. Ray-tracing assumes that effects related to the wave nature of the light can be neglected so that light propagation can be described in terms of rays. The path of the rays is calculated by reflection and refraction. Refraction is defined by Snell's Law of Refraction, which describes the refraction of a ray at a surface separating two media with different refractive indices. As the light rays travel through the model eye, the ray-tracing process calculates the intersections between rays and surfaces, as well as the surface normals at those points, thus determining the new direction of the ray according to Snell's Law. The points and surface normals at the points can be used to determine the shape of a surface.

In certain embodiments, computer 20 applies the ray-tracing process to determine the shape of posterior corneal surface 42 of eye 12 by: (1) defining rays, where each ray is traced from a camera 22, through anterior corneal surface 40 and posterior corneal surface 42, to a part of the eye; (2) determining constraints for the rays, where the constraints are calculated according to the shape of anterior corneal surface 40 and to locations of the features of a part of eye 12; and (3) optimizing parameters according to the constraints, where the optimized parameters describing the shape of the posterior corneal surface. Computer 20 may output a description of the shape via interface 25. The description may be in the form of a map of the surface, such as an axial, tangential, refractive power, or elevation map. The ray tracing process is described in more detail with reference to FIG. 3. Remaining reference numbers of FIG. 1 are described below.

Figure 3:
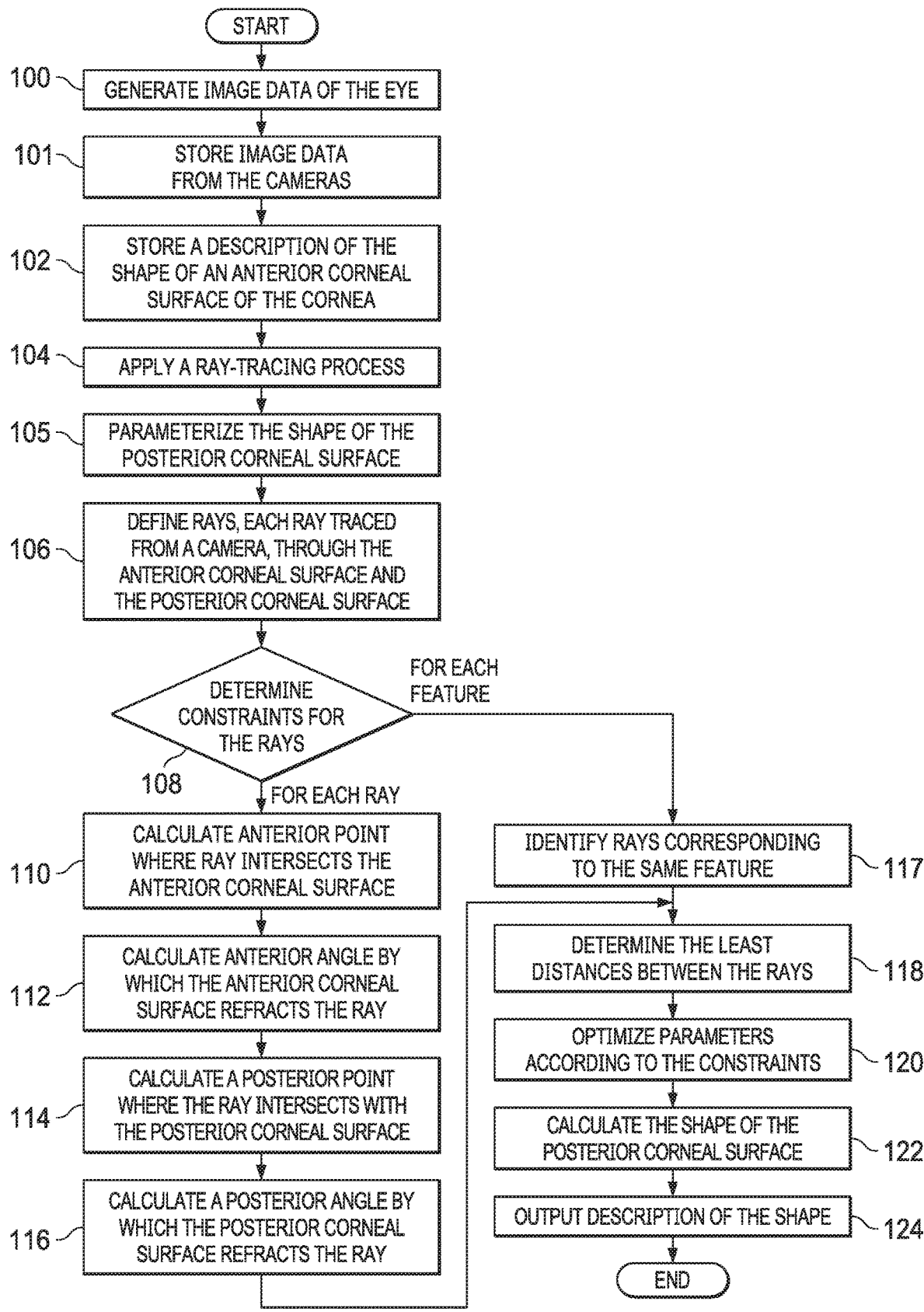
FIG. 3 illustrates an example of a method that measures the posterior corneal surface of an eye that may be performed by the system of FIG. 1.

FIG. 3 illustrates an example of a method that measures posterior corneal surface 42 of eye 12 that may be performed by system 10 of FIG. 1. The method starts at step 100, where cameras 22 receive light reflected from eye 12 and generate image data in response to the reflected light at step 100. The image data describes eye 12, including features of a part of eye 12 posterior to the cornea. In this example, the part is iris 36. Memory 26 of computer 20 stores image data 27 from cameras 22 at step 101, and stores a description 28 of the shape of anterior corneal surface 40 of cornea 34 at step 102.

At step 104, computer 20 applies a ray-tracing process to determine the shape of posterior corneal surface 42. Steps 105 to 120 describe the ray-tracing process. The shape of posterior corneal surface 42 is initially parameterized (i.e., expressed in terms of parameters) at step 105. The initial parameterization is the starting assumption of the shape, so surface 42 may be initially parameterized by selecting values for the parameters that are average values for a population. The shape may be parameterized using biconic, aspheric, or Zernike polynomial based functions. Rays 50 are defined at step 106. In this example method, a ray 50 is traced from a camera 22, through anterior corneal surface 40 and posterior corneal surface 42, to iris 36. For example, a specific ray 50a is traced from a camera 22a, through a point 52a of anterior corneal surface 40 and point 58a of posterior corneal surface 42, to a feature 44a of iris 36.

Constraints for rays 50 are calculated at step 108. A constraint is a requirement (e.g., calculated from known data) that is used to determine the value of one or more parameters. In this example, the constraints calculated according to known data, i.e., the shape of anterior corneal surface 40 in description 28, the position and orientation of the camera 22a, and the locations of features 44 of the part in image data 27. Steps 110 to 116 describe calculating constraints for each ray 50.

For each ray, an anterior point 52 where ray 50 intersects with anterior corneal surface 40 is calculated according to the position of camera 22 relative to eye 12 at step 110. In the example, anterior point 52a where ray 50a intersects with anterior corneal surface 40 is calculated at step 110 according to the position of camera 22a relative to eye 12. More specifically, given a point 54a of camera 22a (e.g., point of image plane of camera 22a) and position of camera 22a relative to eye 12 (e.g., distance from and orientation relative to eye 12), ray 50 can be traced to calculate anterior point 52a. Note that ray 50b traced from point 54b of camera 22b yields a different anterior point 52b. A used herein, "position" refers to the location of an object (e.g., location of the object in x, y, z, space) and the orientation of the object (e.g., direction in which the object is pointing). For each ray 50, an anterior angle 56 by which the anterior corneal surface 40 refracts ray 50 is calculated at step 112 according to the shape of anterior corneal surface 40 at anterior point 52 where ray 50 intersects anterior corneal surface 40. In the example, anterior angle 56a is calculated according to the shape of anterior corneal surface 40 at anterior point 52a using Snell's Law and indices of refraction for parts of eye 12. In the example, anterior angle 56a is expressed relative to ray 50a prior to reaching anterior corneal surface 40. However, anterior angle 56a may be expressed in any suitable manner, e.g., relative to a normal of anterior corneal surface 40 or to a defined coordinate system.

For each ray 50, a posterior point 58 where ray 50 intersects with posterior corneal surface 42 is calculated at step 114 according to the position (e.g., location and orientation) of ray 50 subsequent to the refraction by anterior cornea surface 40. In the example, the position of ray 50a subsequent to the refraction can be calculated from anterior point 52a and anterior angle 56a and estimated thickness of cornea 34.

At step 116, for each ray 50, a posterior angle 60 by which posterior corneal surface 42 refracts the ray is calculated according to the initial assumed shape (from step 105) or the current shape parametrization of the optimization routine (from step 120) of posterior corneal surface 42 at posterior point 58 where ray 50 intersects posterior corneal surface 42. In the example, posterior angle 60a is calculated according to the assumed shape of posterior corneal surface 42 at posterior point 58a using Snell's Law and well-known indices of refraction for parts of eye 12. In the example, posterior angle 60a is expressed relative to ray 50a prior to reaching posterior corneal surface 42. However, posterior angle 60a may be expressed in any suitable manner, e.g., relative to a normal of posterior corneal surface 42 or to a defined coordinate system.

For each feature 44, rays 50 corresponding to the same feature 44 are identified at step 117. Rays 50 corresponding to the same feature 44 are the ones that are traced to the same feature 44 according to steps 110 to 116. In the example, rays 50a-b correspond to the same feature 44a. If the initial parameterization of posterior corneal surface 42 at step 105 were perfect (and if the measurements were ideal), rays 50 corresponding to the same feature 44 from different cameras 22 would intersect at the precise physical location of feature 44. However, the initial parameterization was only an estimate, so rays 50 typically do not intersect at feature 44, but closely bypass each other. The least distance drain represents the closest distance between rays 50, where $d_{min}$=0 represents rays 50 that intersect each other and $d_{min}$>0 represents rays 50 that bypass each other. In these examples, least distance $d_{min}$ for rays 50 corresponding to the same feature 44 typically depend on the imperfections of the measurements and assumptions made for the calculations.

For rays 50 corresponding to the same feature 44, the least distances $d_{min}$ with respect to each other are determined at step 118 from images from at least two cameras 22. In the example, for rays 50a-b corresponding to the same feature 44a, the least distances $d_{min}$ are calculated from images from cameras 22a-b. For a set of rays 50, least distances $d_{min}$ between each pair of rays 50 of the set can be calculated. These distances can be calculated according to known mathematical procedures of calculating the distance between skew lines. A point 62a where rays 50 corresponding to a feature 44 are closest to each other may also be determined. Point 62a represents the reconstructed physical position of feature 44a.

Parameters describing the shape of posterior corneal surface 42 are optimized according to the constraints at step 120. The shape of posterior corneal surface 42 was initially parameterized at step 105. Optimizing the parameters determines values for the parameters that optimize the agreement between images taken with the cameras 22. For example, the values may minimize the least distances drain, such as minimize the sum of the least distances drain for most or all features 44. Any suitable optimization technique may be used, e.g., the least squares or random sample consensus (RANSAC) method.

The shape of posterior corneal surface 42 is calculated from the optimized parameters at step 122. In general, the functions used in the initial parameterization determines the format of the optimized shape. However, the optimized shape may be translated into any suitable format according to known techniques. For example, the optimized parameters may yield the surface elevation and surface normal at different points of anterior corneal surface 28, where interpolation may be used to calculate the elevation and normal at other points. The shape is output to, e.g., a display or a memory at step 124. The method then ends.

A component (e.g., a computer) of the systems and apparatuses disclosed herein may include an interface, logic, and/or memory, any of which may include hardware and/or software. An interface can receive input to the component, provide output from the component, and/or process the input and/or output. Examples of an interface include a GUI, a display screen, or a data connector. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for measuring a posterior corneal surface of a cornea of an eye, comprising:

a plurality of cameras, each camera configured to generate image data representing a part of the eye posterior to the cornea, the part comprising an iris of the eye, the image data describing locations of a plurality of iris features of the iris, the locations on the iris features serving as landmarks used to align images from each of the plurality of cameras; and a computer comprising:
a memory configured to:
store the image data from the cameras;
store a description of the shape of an anterior corneal surface of the cornea; and
one or more processors configured to apply a ray-tracing process to determine the shape of the posterior corneal surface, the ray-tracing process comprising:
define a plurality of rays, each ray traced from a camera of the plurality of cameras, through the anterior corneal surface and the posterior corneal surface, and to the iris of the eye;
determine a plurality of constraints for the rays, the constraints calculated using the description of the shape of the anterior corneal surface and locations of the iris features of the iris in the image data, the constraints calculated by:
for each ray, calculating a posterior point where the ray intersects with the posterior corneal surface according to a position of the ray subsequent to the refraction by the anterior corneal surface;
assuming a shape of the posterior corneal surface according to the posterior points calculated according to the positions of the rays subsequent to the refraction by the anterior corneal surface; and
for each ray, calculating a posterior angle by which the posterior corneal surface refracts the ray towards the iris according to the assumed shape of the posterior corneal surface at the posterior point where the ray intersects the posterior corneal surface; and
optimize a plurality of parameters according to the constraints, the optimized parameters describing the shape of the posterior corneal surface.

2. The system of claim 1, wherein the processors determine the constraints for the rays by:
for each ray traced from a camera, calculating an anterior point where the ray intersects with the anterior corneal surface according to a position of the camera relative to the eye.

3. The system of claim 1, wherein the processors determine the constraints for the rays by:
for each ray, calculating an anterior angle by which the anterior corneal surface refracts the ray according to the shape of the anterior corneal surface at an anterior point where the ray intersects the anterior corneal surface.

4. The system of claim 1, wherein the processors determine the constraints for the rays by, for each iris feature of the iris in the image data:
identifying the rays corresponding to that iris feature; and
from the image data from at least two cameras, calculating one or more least distances among the rays.

5. The system of claim 1, wherein the processors optimize the parameters according to the constraints by:
identifying values for the parameters, where the values optimize agreement between the image data from the cameras.

6. The system of claim 1, wherein the processors optimize the parameters according to the constraints by:
identifying values for the parameters, where the values minimize a plurality of least distances among the rays.

7. The system of claim 1, wherein the processors optimize the parameters according to the constraints by:
identifying values for the parameters, where the values minimize a sum of a plurality of least distances among the rays.

8. The system of claim 1, wherein the processors further calculate the shape of the posterior corneal surface according to the optimized parameters.

9. A method for measuring a posterior corneal surface of a cornea of an eye, comprising:
generating, by each of a plurality of cameras, image data representing a part of the eye posterior to the cornea, the part comprising an iris of the eye, the image data describing locations of a plurality of iris features of the iris, the locations on the iris features serving as landmarks used to align images from each of the plurality of cameras;
accessing a description of the shape of an anterior corneal surface of the cornea;
applying a ray-tracing process to determine the shape of the posterior corneal surface, the ray-tracing process comprising:
defining a plurality of rays, each ray traced from a camera of the plurality of cameras, through the anterior corneal surface and the posterior corneal surface, and to the iris of the eye;
determining a plurality of constraints for the rays, the constraints calculated using the description of the shape of the anterior corneal surface and locations of the iris features of the iris in the image data, the constraints calculated by:
for each ray, calculating a posterior point where the ray intersects with the posterior corneal surface according to a position of the ray subsequent to the refraction by the anterior corneal surface;
assuming a shape of the posterior corneal surface according to the posterior points calculated according to the positions of the rays subsequent to the refraction by the anterior corneal surface; and
for each ray, calculating a posterior angle by which the posterior corneal surface refracts the ray towards the iris according to the assumed shape of the posterior corneal surface at the posterior point where the ray intersects the posterior corneal surface; and
optimizing a plurality of parameters according to the constraints, the optimized parameters describing the shape of the posterior corneal surface.

10. The method of claim 9, wherein determining the constraints for the rays comprises:
for each ray traced from a camera, calculating an anterior point where the ray intersects with the anterior corneal surface according to a position of the camera relative to the eye.

11. The method of claim 9, wherein determining the constraints for the rays comprises:
for each ray, calculating an anterior angle by which the anterior corneal surface refracts the ray according to the shape of the anterior corneal surface at an anterior point where the ray intersects the anterior corneal surface.

12. The method of claim 9, wherein determining the constraints for the rays comprises, for each iris feature of the iris in the image data:
   identifying the rays corresponding to that iris feature; and
   from the image data from at least two cameras, calculating one or more least distances among the rays.

13. The method of claim 9, wherein optimizing the parameters according to the constraints comprises:
   identifying values for the parameters, where the values minimize a plurality of least distances among the rays.

* * * * *